United States Patent

Kimura et al.

Patent Number: 5,266,193
Date of Patent: Nov. 30, 1993

[54] SYRINGE TYPE COLUMN FOR CHROMATOGRAPHY

[75] Inventors: Masaru Kimura, Okayama; Hiromi Kochi, Fukuyama, both of Japan

[73] Assignee: Manac Inc., Hiroshima, Japan

[21] Appl. No.: 932,972

[22] Filed: Aug. 20, 1992

Related U.S. Application Data

[60] Division of Ser. No. 764,974, Sep. 23, 1991, Pat. No. 5,186,839, which is a continuation of Ser. No. 459,828, Jan. 26, 1990, abandoned.

[30] Foreign Application Priority Data

Jun. 3, 1988 [WO] World Int. Prop. O. ............ PCT/JP88/00539

[51] Int. Cl.$^5$ .................................. B01D 15/08
[52] U.S. Cl. ........................ 210/198.2; 210/656; 604/190
[58] Field of Search ............ 210/635, 565, 198.2, 210/416.1, 472; 604/187, 190; 128/218; 436/161, 178; 422/70, 100, 101

[56] References Cited

U.S. PATENT DOCUMENTS

| | | | |
|---|---|---|---|
| 3,493,503 | 2/1970 | Mass | 604/190 |
| 3,810,545 | 5/1974 | Fitz et al. | 210/198.2 |
| 3,859,999 | 1/1975 | Ishikawa | 604/190 |
| 3,902,849 | 9/1975 | Barak et al. | 210/198.2 |
| 3,976,529 | 8/1976 | Weichselbaum | 604/190 |
| 4,008,718 | 2/1977 | Pitesky | 604/190 |
| 4,061,143 | 12/1977 | Ishikawa | 604/190 |
| 4,168,147 | 9/1979 | Acuff | 436/161 |
| 4,214,993 | 7/1980 | Forsythe et al. | 210/198.2 |
| 4,238,197 | 12/1980 | Eisentraut et al. | 436/178 |
| 4,270,921 | 6/1981 | Graas | 210/198.2 |
| 4,341,635 | 7/1982 | Golias | 210/198.2 |
| 4,448,206 | 5/1984 | Martell | 604/190 |
| 4,572,210 | 2/1986 | McKinnon | 604/190 |
| 4,596,561 | 6/1986 | Meyer et al. | 604/190 |
| 4,660,569 | 4/1987 | Etherington | 604/190 |
| 4,732,162 | 3/1988 | Martell | 604/190 |
| 4,787,971 | 11/1988 | Donald | 210/198.2 |
| 4,820,276 | 4/1989 | Moreno | 604/190 |
| 4,891,133 | 1/1990 | Colvin, Jr. | 210/198.2 |
| 4,892,710 | 1/1990 | Wong | 436/178 |
| 4,936,315 | 6/1990 | Lineback | 128/765 |
| 4,973,450 | 11/1990 | Schluter | 436/178 |

FOREIGN PATENT DOCUMENTS 57-158553 9/1982 Japan .................. 210/1982

*Primary Examiner*—Ernest G. Therkorn
*Attorney, Agent, or Firm*—Frishauf, Holtz, Goodman & Woodward

[57] ABSTRACT

A syringe type column used for liquid chromatography, wherein a stationary phase (4) and a solvent for development (5) are placed in a cylindrical barrel (1), and an air vent (2a) extends through a plunger (2) which is inserted in the barrel. Development is effected, while the air vent (2a) is closed to prevent air leakage therethrough, by pushing down the plunger (2). When the plunger (2) is drawn out in order to supplement the solvent for development, air flows into the cylindrical barrel (1) through the air vent (2a) so that an inner space of the barrel (1) is not held under a negative pressure and the stationary phase (4) is not disturbed.

9 Claims, 2 Drawing Sheets

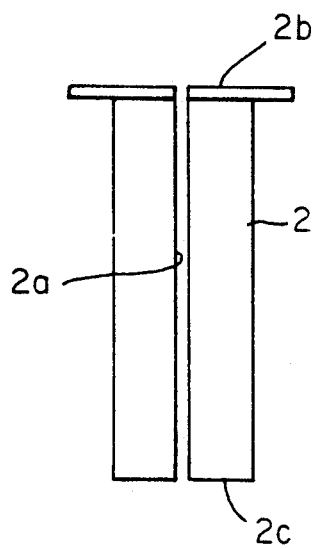
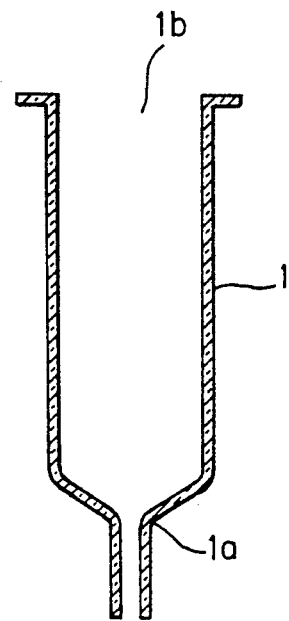
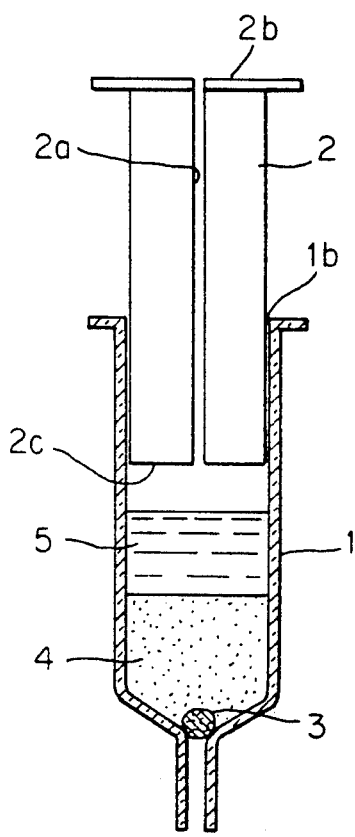
Fig. 2
Fig. 1
Fig. 3

SYRINGE TYPE COLUMN FOR CHROMATOGRAPHY

This is a division of application Ser. No. 07/764,974 filed Sept. 23, 1991, now U.S. Pat. No. 5,186,839 which is a continuation of Ser. No. 07/459,828 filed Jan. 26, 1990, now abandoned.

BACKGROUND OF THE INVENTION

This invention relates to a syringe type column to be used for chromatography, and more particularly to a syringe type column having a novel structure, in which the uniformity in a stationary phase filled in a column may not be disturbed even after repeating operations of introducing a solvent for development thereto, so that the stationary phase filled in the column may not be disorganized or disturbed even after performing operations where high separating efficiency are required.

With recently required precision of chemical reactions, development of simple and convenient methods for purifying or separating a trace of a reaction product is becoming desideratum. As one of such methods, there has been contemplated a pressurized chromatography technique applied with a medium pressure in which a syringe is used as a column. In this method, a barrel of the syringe having a discharge port at the tip is first filled with a silica gel granule, an alumina granule or a cellulose fiber, to which a predetermined amount of a solution containing the reaction product to be separated is then introduced, and further a predetermined amount of a solvent for development. Subsequently, a plunger is inserted in the barrel to be pressed thereinto gradually to effect development and separation of a desired object, which is sampled from the discharge port of the barrel.

When high separating efficiency is tried to be obtained using this method, the following inconvenience occurs.

For the purification or separation of the reaction product, it is generally necessary to introduce the solvent for development repeatedly to the stationary phase while uniformly maintaining it in the filled state. However, in the above method, the plunger must be drawn out of the barrel every time the solvent for development is introduced into the barrel. When the plunger is drawn out of the barrel, an inner space of the barrel inevitably suffers a negative pressure, so that the air flows into the barrel through the discharge port at the tip thereof, and the filled state of the stationary phase is subject to turbulence due to the movement of the air flowing into the barrel to break down an equilibrium state formed therein.

It is an object of this invention to provide a syringe-type column having a structure in which the solvent for development can repeatedly be introduced into the column while the equilibrium state formed in the stationary phase is maintained and without causing the inconvenience as described above in said repeated introduction of the solvent for development.

SUMMARY OF THE INVENTION

The syringe type column of this invention comprises a cylindrical barrel having a solution discharge port at one end and an opening at the other end; and a plunger which is inserted from the open end of the cylindrical barrel and has at least one air vent formed to extend therethrough along the direction of an axis thereof.

BRIEF DESCRIPTION OF THE DRAWINGS

FIG. 1 shows, in longitudinal cross-section, a cylindrical barrel which is one member of the column of this invention;

FIG. 2 shows, in longitudinal cross-section, a plunger which is the other member of the column of this invention;

FIG. 3 is an illustration for explaining the operation of the column of this invention.

DETAILED DESCRIPTION

Figure 4:
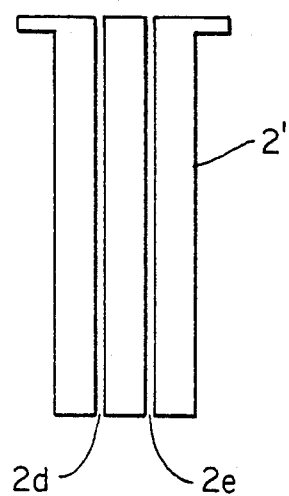
FIG. 4 shows another embodiment of the plunger of this invention.

The column of this invention will now be described in more detail referring to the drawings. FIG. 1 and FIG. 2 show, in longitudinal cross-section, the cylindrical barrel and the plunger, respectively, which constitute a column when they are combined with each other.

The cylindrical barrel 1 has, on the whole, for example, a cylindrical shape, wherein the solution discharge port 1a is provided at a bottom end and wherein an upper end is defined as the open end 1b. The plunger 2 has at least one air vent 2a formed to pierce or extend therethrough along the longitudinal axis thereof from an upper surface 2b to a lower surface 2c.

The column of this invention is operated as follows: As shown in FIG. 3, the outlet of the solution discharge port 1a of the cylindrical barrel 1 is sealed with a liquid-permeable member 3 such as cotton. Next, a predetermined amount of a stationary phase 4 is filled into the barrel 1. As the stationary phase 4, a suitable one may be selected depending on the purpose from those used for ordinary column chromatography and HPLC. Subsequently, a predetermined amount of sample solution is introduced from the open end 1b and then a predetermined amount of a solvent for development 5 is further introduced.

The plunger 2 is then inserted in the open end 1b to be pressed into the barrel 1 with finger pressure of an operator being applied to the upper surface 2b thereof.

As the plunger 2 is pressed into the barrel 1, the solvent for development 5 permeates through the stationary phase 4, whereby a desired object can gradually be eluted. When the lower surface 2c of the plunger 2 substantially comes into abutment against an upper surface of the stationary phase 4 after consumption of the solvent for development 5, the finger applied to the upper surface 2b of the plunger 2 is released to draw out the plunger 2.

In the above drawing-out process, air flows into the barrel 1 through the air vent 2a, so that an inner space of the barrel 1 will never suffer negative pressure. Moreover, since the air flows in not through the solution discharge port 1a but through the air vent 2a of the plunger 2, the stationary phase 4 will never be subject to turbulence due to the movement of the in-flowing air.

FIG. 4 shows another embodiment of the plunger 2' in which two air vents 2d and 2e are formed to pierce or extend therethrough. In the plunger 2' of this embodiment, the solvent for development 5 can be introduced into the barrel 1 through the other air vent 2e without drawing out the plunger 2' therefrom.

The cylindrical barrels 1 and plungers 2, 2' may be made of glass or a resin such as polyethylene.

As is apparent from the above description, the column of this invention has very high practical value, since the solvent for development 5 can be introduced thereinto repeatedly without breaking down the equilibrium state formed in the stationary phase 4 to thereby obtain high efficiency of separating the desired object.

We claim:

1. A syringe type column for use in chromatography sized and dimensioned for separation of a reaction product, comprising:

a generally cylindrical barrel having a solution discharge port at one end and an opening at another end thereof and a stationary phase suitable for ordinary column chromatography or HPLC uniformly filled in said barrel;

a liquid-permeable member closing said solution discharge port to the passage of the stationary phase;

a source of liquid solvent for development;

said barrel having respective volumes therein to be occupied with a stationary phase, a sample liquid solution containing a trace substance to be purified or separated therefrom, and a liquid solvent for development; and a plunger which is repeatably insertable into and repeatably removable from said barrel, said plunger having at least one air vent formed therein, said at least one air vent extending through said plunger in a longitudinal direction of said plunger, said at least one air vent communicating the interior of said barrel with the outside of said barrel;

said at least one air vent being manually closable by an operator during insertion of said plunger into said barrel to cause said solvent for development to permeate through said stationary phase, and said at least one air vent being manually operable by the operator during drawing out of said plunger from said barrel for allowing air to flow into the interior of said barrel through said at least one air vent when said plunger is drawn out from said barrel and for thereby preventing said stationary phase from being subjected to turbulence due to the movement of in-flowing air through said solution discharge port during said drawing out of said plunger from said barrel.

2. The syringe type column of claim 1, wherein said plunger has a longitudinal axis, and said at least one air vent extends along said longitudinal axis.

3. The syringe type column of claim 1, wherein said plunger has a longitudinal axis, and said at least one air vent extends substantially parallel to said longitudinal axis.

4. The syringe type column of claim 1, wherein said plunger has an outer surface portion in sliding sealing contact with inner walls of said cylindrical barrel.

5. The syringe type column of claim 1, wherein said plunger has at least two spaced apart air vents formed therein and which extend therethrough in a longitudinal direction thereof.

6. The syringe type column of claim 5, wherein said plunger has a longitudinal axis, and said at least two air vents extend substantially parallel to said longitudinal axis.

7. The syringe type column of claim 5, wherein said plunger has an outer surface portion in sliding sealing contact with inner walls of said cylindrical barrel.

8. The syringe type column of claim 5, wherein said at least two air vents extend completely through said plunger from one end surface to an opposite end surface thereof.

9. The syringe type column of claim 1, wherein said at least one air vent extends completely through said plunger from one end surface to an opposite end surface thereof.

* * * * *